(12) United States Patent
Zou et al.

(10) Patent No.: US 11,517,602 B2
(45) Date of Patent: *Dec. 6, 2022

(54) TRADITIONAL CHINESE MEDICINE COMPOSITION FOR IMPROVING BONE HEALTH AND PREPARATION AND USES THEREOF

(71) Applicant: Chenland Nutritionals Inc., Pomona, CA (US)

(72) Inventors: Shengcan Zou, Qingdao (CN); Zengliang Zhang, Qingdao (CN); Jiancheng Zong, Qingdao (CN); Wenyu Li, Qingdao (CN); Xin Li, Qingdao (CN); Li Li, Qingdao (CN); Shanglong Wang, Qingdao (CN); Lei Zong, Qingdao (CN)

(73) Assignee: Chenland Nutritionals Inc.

(*) Notice: Subject to any disclaimer, the term of this patent is extended or adjusted under 35 U.S.C. 154(b) by 11 days.

This patent is subject to a terminal disclaimer.

(21) Appl. No.: 17/035,808

(22) Filed: Sep. 29, 2020

(65) Prior Publication Data

US 2021/0069275 A1 Mar. 11, 2021

Related U.S. Application Data

(63) Continuation of application No. PCT/CN2020/098771, filed on Jun. 29, 2020.

(30) Foreign Application Priority Data

Mar. 12, 2020 (CN) .......................... 202010171209.X
Jun. 22, 2020 (CN) .......................... 202010575023.0

(51) Int. Cl.
*A61K 36/46* (2006.01)
*A61P 19/10* (2006.01)
*A61K 36/11* (2006.01)
*A61K 36/39* (2006.01)
*A23L 33/105* (2016.01)
*B01D 11/02* (2006.01)
*A23L 33/00* (2016.01)

(52) U.S. Cl.
CPC ............ *A61K 36/46* (2013.01); *A23L 33/105* (2016.08); *A23L 33/40* (2016.08); *A61K 36/11* (2013.01); *A61K 36/39* (2013.01); *A61P 19/10* (2018.01); *B01D 11/0288* (2013.01); *A23V 2002/00* (2013.01); *A61K 2236/17* (2013.01); *A61K 2236/333* (2013.01); *A61K 2236/50* (2013.01); *A61K 2236/51* (2013.01)

(58) Field of Classification Search
None
See application file for complete search history.

(56) References Cited

FOREIGN PATENT DOCUMENTS

| CN | 101288686 A | * | 10/2008 |
| CN | 104224888 A | * | 12/2014 |
| CN | 104800706 A | * | 7/2015 |

OTHER PUBLICATIONS

"Dextrin" (Dextrin Handling/Processing, Technical Evaluation Report (Oct. 12, 2011), Complied by the Technical Services Branch for the USDA National Organic Program, 12 pages).*

* cited by examiner

Primary Examiner — Susan Hoffman (57) ABSTRACT

A traditional Chinese medicine composition includes 60%-80% by weight of *Eucommia ulmoides* extract, 15%-30% by weight of *Rhizoma Drynariae* extract and 5%-10% by weight of *Semen Cuscutae* extract. A method of preparing the traditional Chinese medicine composition is also provided. Uses of the traditional Chinese medicine composition in the prevention and/or treatment of osteoporosis are also provided.

5 Claims, 5 Drawing Sheets

TRADITIONAL CHINESE MEDICINE COMPOSITION FOR IMPROVING BONE HEALTH AND PREPARATION AND USES THEREOF

TECHNICAL FIELD

The present disclosure relates to natural medicines, and more particularly to a traditional Chinese medicine composition for improving bone health and preparation and uses thereof.

BACKGROUND

The changes in human dietary structure and the prolongation of average life expectancy bring an increase in the level of the population aging in China, and osteoporosis has gradually become one of the main diseases threatening the life and health of middle-aged and elderly people. The osteoporosis is pathologically characterized by decreased bone mass and damaged bone tissue microstructure, which will further give rise to many systemic osteoporosis-related symptoms, such as increased bone fragility, decreased bone density and fracture Currently, there are more than 200 million cases worldwide suffering from osteoporosis, and its incidence has jumped to the sixth place among the common and frequently-occurring diseases. China has the most osteoporosis patients in the world (more than 90 million). Osteoporosis seriously affects the life and health of middle-aged and elderly people due to its high morbidity, disability and mortality, and has gradually become a threat to the public health.

Currently, drugs for the prevention and adjuvant treatment of osteoporosis mainly include drugs for promoting bone growth, such as growth hormone and estrogen; and drugs for inhibiting bone resorption, such as calcitonin and bisphosphonates. However, these drugs all show obvious side effects, for example, the long-term use of estrogen will lead to an increased risk of endometrial cancer and breast cancer. Therefore, available drugs are not very suitable for the long-term treatment of osteoporosis.

Given the above, there is an urgent need for those of ordinary skill in the art to develop a traditional Chinese medicine composition for treating osteoporosis and promoting bone health with reduced toxic and side effects and high adsorption.

SUMMARY

In view of the above, an object of the present disclosure is to provide a traditional Chinese medicine composition for improving bone health to overcome the defects in the prior art, where the traditional Chinese medicine composition has no toxic side effects and high adsorption, and can be used as a dietary supplement or a health-care food ingredient to prevent and treat osteoporosis and promote bone health.

Technical solutions of the present disclosure are specifically described as follows.

Traditional Chinese medicine scholars propose that the pathogenesis of osteoporosis is closely associated with "kidney deficiency", and *Eucommia ulmoides*, *Rhizoma Drynariae* and *Semen Cuscutae* have the effects of invigorating the liver and kidney and strengthening the bones and muscles, so these medicinal materials are commonly used in clinic for strengthening the kidney and bones and exhibit good therapeutic effects. However, there is no report about the combination of *Eucommia ulmoides*, *Rhizoma Drynariae* and *Semen Cuscutae* for the treatment of osteoporosis. The disclosure combines *Eucommia ulmoides*, *Rhizoma Drynariae* and *Semen Cuscutae* based on the compatibility theory of traditional Chinese medicine to develop a composition with an excellent mix ratio that can improve osteoporosis and promote bone health.

In a first aspect, the disclosure provides a traditional Chinese medicine composition for improving bone health, comprising:
60%-80% by weight of *Eucommia ulmoides* extract;
15%-30% by weight of *Rhizoma Drynariae* extract; and
5%-10% by weight of *Semen Cuscutae* extract.

In an embodiment, the traditional Chinese medicine composition comprises:
60%-70% by weight of *Eucommia ulmoides* extract;
20%-30% by weight of *Rhizoma Drynariae* extract; and
8%-10% by weight of *Semen Cuscutae* extract.

In an embodiment, the traditional Chinese medicine composition comprises:
60% by weight of *Eucommia ulmoides* extract;
30% by weight of *Rhizoma Drynariae* extract; and
10% by weight of *Semen Cuscutae* extract.

In an embodiment, the above extracts are separately extracted from the corresponding traditional Chinese medicine material, and the traditional Chinese medicine composition is prepared by extracting the above extracts respectively from *Eucommia ulmoides*, *Rhizoma Drynariae* and *Semen Cuscutae* and compounding.

It should be noted that, according to the crude drug dosage recommended by the pharmacopoeia, a dosage of the traditional Chinese medicine composition prepared herein is 0.5-2.0 g, and an effective dosage of the traditional Chinese medicine composition is determined by subsequent animal experiments.

Moreover, the raw materials of the extracts used herein are scientifically selected (based on prescriptions related to bone health) and combined organically according to the compatibility of traditional Chinese medicines rather than simple superimposing of the effect of each Chinese medicine. Effects of the abovementioned traditional Chinese medicine materials are listed as follows:

*Eucommia ulmoides*
Characteristics: sweet in, taste and warm in nature;
Functions: invigorating liver and kidney, strengthening muscles and bones and preventing miscarriage;
Indications: lumbar spine pain, foot and knee weakness, dribbling urination, vaginal itch and wetness, fetal leakage, fetal, restlessness and high blood pressure.

*Rhizoma Drynariae*
Functions: healing and relieving pain, invigorating the kidney and strengthening bones and external use to disperse wind and eliminate freckle.
Indications: sprain and contusion, bone fracture, kidney deficiency, low back pain, muscle and bone weakness, tinnitus and deafness, loose teeth and external treatment of alopecia areata and vitiligo.

*Semen Cuscutae*
Functions: replenishing liver and kidney, consolidating essence and reducing urination, preventing miscarriage, improving eyesight, stopping diarrhea and external use to eliminate wind and freckle.
Indications: liver and kidney deficiency, waist and knee weakness impotence and nocturnal emission, enuresis, frequent urination, kidney deficiency fetal leakage, fetal restlessness, dysopia, spleen and kidney deficiency and diarrhea and external use for vitiligo.

It can be seen from above that though *Eucommia ulmoides* and *Rhizoma Drynariae* both can strengthen muscles and bones, they still have their own emphasis. Specifically, *Eucommia ulmoides* focuses on nourishing the liver and kidney and strengthening the bones and muscles. It has been mentioned in the traditional Chinese medicine theory that the kidney stores essence and dominates bone to produce marrow, so if the kidney essence is sufficient, the bone marrow is active, and bones are strong and powerful; and if the kidney essence is deficient, the bone marrow is depleted, and bones lose oxygen and become fragile and weak. Therefore, the bone health is closely associated with the kidney health. *Rhizoma Drynariae* focuses on relieving pain and healing injury, invigorating the kidney and essence and strengthening waist and bones, and is commonly used for treating bone diseases in clinic. *Semen Cuscutae* shows effects of nourishing liver and kidney and dispelling rheumatism.

Recently, it has been found that the total flavonoids of *Eucommia ulmoides* can promote the synthesis of type I collagen by osteoblasts; *Rhizoma Drynariae* can increase bone strength, inhibit bone resorption and promote the bone, formation; and the flavonoids of *Semen Cuscutae* play a role in promoting the intestinal absorption for calcium and improving the density of loosen bones. The combination of the three medicine materials is made based on the complementarities in function rather than simple superimposition of functions.

In addition, though the common dosage of each traditional Chinese medicine is known in the prior art, the prescription of the disclosure is made for the target disease by organically combining the above medicines, and its medicinal effect is not equivalent to the simple superposition of the effects of these medicines at a commonly-used amount. Actually, it cannot determine the amount of each medicine in the prescription according to their individual commonly-used amount, and the compounding ratio depends on many factors such as the characteristics of the medicinal materials and the compatibility of monarch drugs, ministerial drugs, adjuvant drugs and envoy drugs, and cannot be determined by experimental means such as comparison method and orthogonal test.

In a second aspect, the disclosure provides a method of preparing the above traditional Chinese medicine composition, comprising:

subjecting *Eucommia ulmoides*, *Rhizoma Drynariae* and *Semen Cuscutae* to extraction, purification, concentration and drying to produce *Eucommia ulmoides* extract, *Rhizoma Drynariae* extract and *Semen Cuscutae* extract, respectively; and mixing the *Eucommia ulmoides* extract, the *Rhizoma Drynariae* extract and the *Semen Cuscutae* extract uniformly to produce the traditional Chinese medicine composition;

wherein the method specifically comprises:

(1.1) subjecting *Eucommia ulmoides* to extraction with an ethanol solution under refluxing and filtration; subjecting a residue to extraction with a solvent and filtration several times; and combining filtrates to obtain an *Eucommia ulmoides* filtrate;

(1.2) subjecting *Rhizoma Drynariae* to extraction with an ethanol solution under refluxing and filtration; subjecting a residue to extraction with a solvent and filtration several times; and combining filtrates to obtain a *Rhizoma Drynariae* filtrate;

(1.3) subjecting *Semen Cuscutae* to extraction with an ethanol solution under refluxing and filtration; subjecting a residue to extraction with a solvent and filtration several times; and combining filtrates to obtain a *Semen Cuscutae* filtrate;

(2) subjecting the *Eucommia ulmoides* filtrate, the *Rhizoma Drynariae* filtrate and the *Semen Cuscutae* filtrate to purification, concentration, spray drying or vacuum drying and sieving to produce an *Eucommia ulmoides* extract, a *Rhizoma Drynariae*, extract and a *Semen Cuscutae* extract; and (3) mixing the *Eucommia ulmoides* extract, the *Rhizoma Drynariae* extract and the *Semen Cuscutae* extract uniformly in a weight ratio of (60-80):(15-30):(5-10) to produce the traditional Chinese medicine composition.

In an embodiment, in step (3), the weight ratio of the *Eucommia ulmoides* extract to the *Rhizoma Drynariae* extract to the *Semen Cuscutae* extract is (60-70):(20-30):(8-10), preferably 60:30:10.

In an embodiment, in step (1), a volume ratio of *Eucommia ulmoides* to the ethanol solution is 1:(5-20); a volume ratio of *Rhizoma Drynariae* to the ethanol solution is 1:(5-20); a volume ratio of *Semen Cuscutae* to the ethanol solution is 1:(5-20); and the extraction of *Eucommia ulmoides*, *Rhizoma Drynariae* and *Semen Cuscutae* is performed at 80-100° C. 1-3 times each for 1-3 h, respectively.

In an embodiment, in step (1), a volume ratio of the solvent to the residue is (6-8):1; and the extraction of the residue is performed at 80-100° C. under refluxing 0-3 times each for 1-2 h.

In an embodiment, in step (1), the solvent is deionized water or an ethanol solution.

In an embodiment, in step (2), the spray drying is performed at 180-200° C.; the vacuum drying is performed at 50-100° C.; and the sieving is performed using a sieve of 60-80 mesh.

In an embodiment, step (2) further comprises:

before the spray drying or the vacuum drying, introducing dextrin to the concentrated *Eucommia ulmoides* product, the concentrated *Rhizoma Drynariae* product and the concentrated *Semen Cuscutae* product, respectively, followed by mixing uniformly;

wherein the dextrin is 1%-20% by weight of *Eucommia ulmoides*, *Rhizoma Drynariae* and *Semen Cuscutae*, respectively.

In an embodiment, the method comprises:

(1) subjecting *Eucommia ulmoides* to extraction with a 60%-80% ethanol solution in a volume ratio of 1:(5-20) under refluxing for 1-3 h and filtration to obtain a residue; subjecting the residue to extraction with deionized water in a volume ratio of 1:(6-8) under refluxing 2-3 times each for 1-2 h and filtration; combining filtrates followed by concentration; adding maltodextrin and continuously concentrating the combined filtrate to a density of 1.15-1.2; and drying the concentrated product at 50-100° C. under vacuum followed by sieving with a sieve of 80 mesh to produce the *Eucommia ulmoides* extract; where the maltodextrin is 5% by weight of *Eucommia ulmoides*;

(2) subjecting *Rhizoma Drynariae* to extraction with a 60%-80% ethanol solution in a volume ratio of 1:(5-20) under refluxing for 1-3 h and filtration to obtain a residue; subjecting the residue to extraction with 60%-80% ethanol solution in a volume ratio of 1:(6-8) under refluxing 2-3 times each for 1-2 h and filtration; combining filtrates followed by concentration; adding maltodextrin and continuously concentrating the combined filtrate to a density of 1.2; and drying the concentrated product at 50-100° C. under vacuum followed by sieving with a sieve of 80 mesh to produce the *Rhizoma Drynariae* extract; where the maltodextrin is 10% by weight of *Rhizoma Drynariae;*

(3) subjecting *Semen Cuscutae* to immersion in a 60%-80% ethanol solution in a volume ratio of 1:(5-20) for 10-60 min, extraction under refluxing for 1-3 h and filtration to obtain a residue; subjecting the residue to extraction with 60%-80% ethanol solution in a volume ratio of 1:(6-8) under refluxing 2-3 times each for 1-2 h and filtration; combining filtrates followed by concentration to a density of 1.12-1.15; and subjecting the concentrated product to spray drying at 180-200° C. followed by sieving with a sieve of 80 mesh to produce the *Semen Cuscutae* extract; and (4) mixing the *Eucommia ulmoides* extract, the *Rhizoma Drynariae* extract and the *Semen Cuscutae* extract uniformly according to the above weight ratio to produce the traditional Chinese medicine composition.

In an embodiment, in step (1), the *Eucommia ulmoides* is subjected to extraction, once with a 75%-80% ethanol solution in a volume ratio of 1:6 for 2 h; the residue is subjected to extraction with deionized water in a volume ration, of 1:6 under refluxing twice each for 1.5 h; and the vacuum drying is performed at 75° C.;

in step (2), the *Rhizoma Drynariae* is subjected to extraction with a 75% ethanol solution three times respectively in a volume ratio of 1:6, 1:5 and 1:5 under refluxing each for 2 h; and the vacuum drying is performed at 75° C.; and, in step (3), the *Semen Cuscutae* is subjected to extraction with a 75% ethanol solution three times respectively in a volume ratio of 1:6, 1:5 and 1:5 under refluxing, each for 2 h; and the spray drying is performed at 180° C.

In a third aspect, the disclosure further provides a method of treating osteoporosis in a patient in need thereof, comprising:

administering an effective amount of the above traditional Chinese medicine composition to the patient;

In an embodiment, the traditional Chinese medicine composition is used as a dietary supplement or a health-care food; and the traditional Chinese medicine composition is in a form of a capsule, a granule or a tablet.

Compared to the prior art, the disclosure has the following beneficial effects.

(1) Traditional Chinese medicine scholars propose that the pathogenesis of osteoporosis is closely associated with "kidney deficiency", and *Eucommia ulmoides, Rhizoma Drynariae* and *Semen Cuscutae* have the effects of invigorating the liver and kidney and strengthening the bones and muscles, so these medicinal materials are commonly used in clinic for strengthening the kidney and bones and exhibit good therapeutic effects. However, there is no report about the combination of *Eucommia ulmoides, Rhizoma Drynariae* and *Semen Cuscutae* for the treatment of osteoporosis. The disclosure combines *Eucommia ulmoides, Rhizoma Drynariae* and *Semen Cuscutae* based on the compatibility theory of traditional Chinese medicine to develop a composition with an excellent mix ratio that can improve osteoporosis and promote bone health.

(2) The disclosure employs a preparation process of separate extraction and compounding, and, determines that flavonoids are the main active substances in each extract. Compared to the traditional extraction process, the disclosure has better quality of the extract and higher controllability.

(3) The composition of the disclosure is confirmed by pharmacological experiment to have desirable effects of improving osteoporosis and bone health.

(4) The composition provided herein has no toxic side effects and high adsorption, and can be used to treat osteoporosis and improve bone health. Therefore, the composition of the disclosure can not only improve the bone health of middle-aged and elderly people, but also effectively avoid diseases caused by osteoporosis.

BRIEF DESCRIPTION OF THE DRAWINGS

The drawings used in the embodiments will be briefly described to make the technical solutions of the disclosure clearer. Obviously, the embodiments illustrated in the drawings are merely part of the embodiments of the disclosure, and other drawings obtained by those skilled in the art without sparing any creative effort should fall within the scope of the invention.

DETAILED DESCRIPTION OF EMBODIMENTS

Technical solutions of the present disclosure will be clearly and completely described below with reference to the embodiments. Obviously, described below are merely some embodiments of the disclosure, which are not intended to limit the disclosure. Other embodiments made by those skilled in the art without sparing any creative effort should fall within the scope of the disclosure.

The disclosure provides a traditional Chinese medicine composition, which has no toxic side effects and high adsorption. The composition can improve bone health, and can be used as a dietary supplement or a health food raw material for the prevention or treatment of osteoporosis, and thus it is suitable for commercial promotion.

The invention will be further described below with reference to the embodiments. It should be understood that these embodiments are merely illustrative of the invention, and are not intended to limit the invention. Any improvement and modification made by those skilled in the art without departing from the spirit of the invention should still fall within the scope of the invention.

The disclosure provides a traditional Chinese medicine composition for improving bone health, including:

60%-80% by weight of *Eucommia ulmoides* extract;
15%-30% by weight of *Rhizoma Drynariae* extract; and
5%-10% by weight of *Semen Cuscutae* extract.

In an embodiment, the above extracts are separately extracted from the corresponding traditional Chinese medicine material, and the traditional Chinese medicine composition is prepared by extracting the above extracts respectively from *Eucommia ulmoides, Rhizoma Drynariae* and *Semen Cuscutae* and compounding.

The disclosure also, provides a method of preparing the above traditional Chinese medicine composition, including:

subjecting *Eucommia ulmoides, Rhizoma Drynariae* and *Semen Cuscutae* to extraction, purification, concentration and spray drying to produce *Eucommia ulmoides* extract, *Rhizoma Drynariae* extract and *Semen Cuscutae* extract, respectively; and mixing the *Eucommia ulmoides* extract, the *Rhizoma Drynariae* extract and the *Semen Cuscutae* extract uniformly to produce the traditional Chinese medicine composition;

where the method specifically includes:

(1) subjecting *Eucommia ulmoides*, *Rhizoma Drynariae* and *Semen Cuscutae* to extraction respectively with an ethanol solution under refluxing and filtration; subjecting a residue to extraction with a solvent and filtration several times; and combining filtrates to obtain a crude *Eucommia ulmoides* extract, a crude *Rhizoma Drynariae* extract and a crude *Semen Cuscutae* extract, respectively;

(2) subjecting the crude *Eucommia ulmoides* extract, the crude *Rhizoma Drynariae* extract and the crude *Semen Cuscutae* extract to purification, concentration, spray drying or vacuum drying and sieving to produce the *Eucommia ulmoides* extract, the *Rhizoma Drynariae* extract and the *Semen Cuscutae* extract; and (3) mixing the *Eucommia ulmoides* extract, the *Rhizoma Drynariae* extract and the *Semen Cuscutae* extract uniformly in a weight ratio of (60-80):(15-30):(5-10) to produce the traditional Chinese medicine composition.

In an embodiment, in step (1), a volume ratio of *Eucommia ulmoides* to the ethanol solution is 1:(5-20); a volume ratio of *Rhizoma Drynariae* to the ethanol solution is 1:(5-20); a volume ratio of *Semen Cuscutae* to the ethanol solution is 1:(5-20); and the extraction of *Rhizoma Drynariae*, *Rhizoma Drynariae* and *Semen Cuscutae* is performed at 80-100° C. 1-3 times each for 1-3 h, respectively.

In an embodiment, in step (1), a volume ratio of the solvent to the residue is (6-8):1; and the extraction of the residue is performed at 80-100° C. under refluxing 0-3 times each for 1-2 h.

In an embodiment, in step (2), the spray drying is performed at 180-200° C.; the vacuum drying is performed at 50-100° C.; and the sieving is performed using a sieve of 60-80 mesh.

In an embodiment, step (2) further includes:

before the spray drying or the vacuum drying, introducing a dextrin to the concentrated *Eucommia ulmoides* product, the concentrated *Rhizoma Drynariae* product and the concentrated *Semen Cuscutae* product, respectively, followed by mixing uniformly;

where the dextrin is 1%-20% by weight of *Eucommia ulmoides*, *Rhizoma Drynariae* and *Semen Cuscutae*, respectively.

In a third aspect, the disclosure further provides a method of treating osteoporosis in a patient in need thereof, including:

administering, an effective amount of the above traditional Chinese medicine composition to the patient;

In an embodiment, the traditional Chinese medicine composition is used as a dietary supplement or a health-care food; and the traditional Chinese medicine composition is in a form of a capsule, a granule or a tablet.

Technical solutions of the disclosure will be further described below with reference to the embodiments.

Example 1

Provided herein was a method of preparing a traditional Chinese medicine, for improving bone health, which was specifically described as follows.

(1) *Eucommia ulmoides* was subjected to extraction with a 60%-80% ethanol solution in a volume ratio of 1:6 under refluxing for 2 h and filtration to obtain a residue. The residue was subjected to extraction with deionized water twice in a volume ratio of 1:6 under refluxing each for 1.5 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was crushed and subjected to extraction with a 75% ethanol solution three times respectively in a volume ratio of 1:6, 1:5 and 1:5 under refluxing each for 2 h and filtration. Filtrates were combined, concentrated and added with maltodextrin, where the maltodextrin was 10% by weight of *Rhizoma Drynariae*. Then the combined filtrate was continuously concentrated to a density of 1.2, dried at 75° C. under vacuum and sieved with a sieve of 80 mesh to produce the *Rhizoma Drynariae* extract.

(3) *Semen Cuscutae* was subjected to extraction with a 75% ethanol solution three times respectively in a volume ratio of 1:6, 1:5 and 1:5 under refluxing each for 2 h and filtration. Filtrates were combined, concentrated to a density of 1.12-1.15 and subjected to spray drying at 180° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 60:30:10 to produce the traditional Chinese medicine composition.

Example 2

Provided herein was a method of preparing a traditional Chinese medicine for improving bone health, which was specifically described as follows.

(1) *Eucommia ulmoides* was subjected to extraction With a 85% ethanol solution in a volume ratio of 1:8 under refluxing for 2 h and filtration to obtain a residue and a filtrate. The residue was subjected to extraction with deionized water twice in a volume ratio of 1:6 under refluxing each for 1 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was subjected to extraction with a 80% ethanol solution in a volume ratio of 1:8 under refluxing for 2 h and filtration to obtain a residue. The residue was subjected to extraction with the 80% ethanol solution twice in a volume ratio of 1:6 under refluxing each for 2 h. Filtrates were combined, concentrated and added with maltodextrin, where the maltodextrin was 10% by weight of *Rhizoma Drynariae*. Then the filtrate was continuously concentrated to a density of 1.2, dried at 75° C. under vacuum and sieved with a sieve of 80 mesh to produce the *Rhizoma Drynariae* extract.

(3) *Semen Cuscutae* was immersed in a 80% ethanol solution in a volume ratio of 1:8 for 0.5 h and subjected to extraction under refluxing for 2 h and filtration to obtain, a residue. The residue was subjected to extraction with the 80% ethanol solution in a volume ratio of 1:6 under refluxing twice each for 1 h. Filtrates were combined, concentrated to a density of 1.12-1.15 and subjected to spray drying at 180-200° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 60:30:10 to produce the traditional Chinese medicine composition.

Example 3

Provided herein was a method of preparing a traditional Chinese medicine for improving bone health, which was specifically described as follows.

(1) *Eucommia ulmoides* was subjected to extraction With a 70% ethanol solution in a volume ratio of 1:8 under refluxing for 2 h and filtration to obtain a residue and a filtrate. The residue was subjected to extraction with deionized water twice in a volume ratio of 1:6 under refluxing each for 1 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was subjected to extraction with a 80% ethanol solution in a volume ratio of 1:8 under refluxing for 2 h and filtration to obtain a residue and a filtrate. The residue was subjected to extraction with the 80% ethanol solution twice in a volume ratio of 1:6 under refluxing each for 2 h and filtration. Filtrates were combined, concentrated and added with maltodextrin, where the maltodextrin was 10% by weight of *Rhizoma Drynariae*. Then the combined filtrate was continuously concentrated to a density of 1.2, dried at 75° C. under vacuum and sieved with a sieve of 80 mesh to produce the *Rhizoma Drynariae* extract.

(3) *Semen Cuscutae* was immersed in a 80% ethanol solution in a volume ratio of 1:8 for 0.5 h and subjected to extraction under refluxing for 2 h and filtration to obtain a residue and a filtrate. The residue was subjected to extraction with the 80% ethanol solution in a volume ratio of 1:6 under refluxing twice each for 1 h. Filtrates were combined, concentrated to a density of 1.12-1.15 and subjected to spray drying at 180-200° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 75:15:10 to produce the traditional Chinese medicine composition.

Example 4

Provided herein was a method of preparing a traditional Chinese medicine for improving bone health, which was specifically described as follows.

(1) *Eucommia ulmoides* was subjected to extraction With a 85% ethanol solution in a volume ratio of 1:8 under refluxing for 2 h and filtration to obtain a residue and a filtrate. The residue was subjected to extraction with deionized water twice in a volume ratio of 1:6 under refluxing each for 1 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was subjected to extraction with a 80% ethanol solution in a volume ratio of 1:8 under refluxing for 2 h and filtration to obtain a residue and a filtrate. The residue was subjected to extraction with the 80% ethanol solution twice in a volume ratio of 1:6 under refluxing each for 2 h and filtration. Filtrates were combined, concentrated and added with maltodextrin, where the maltodextrin was 10% by weight of *Rhizoma Drynariae*. Then the combined filtrate was continuously concentrated to a density of 1.2, dried at 75° C. under vacuum and sieved with a sieve of 80 mesh to produce the *Rhizoma Drynariae* extract.

(3) *Semen Cuscutae* was immersed in a 80% ethanol solution in a volume ratio of 1:8 for 0.5 h and subjected to extraction under refluxing for 2 h and filtration to obtain a residue and a filtrate. The residue was subjected to extraction with the 80% ethanol solution in a volume ratio of 1:6 under refluxing twice each for 1 h. Filtrates were combined, concentrated to a density of 1.12-1.15 and subjected to spray drying at 180-200° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 70:20:10 to produce the traditional Chinese medicine composition.

Example 5

Provided herein was a method of preparing a traditional Chinese medicine for improving bone health, which was specifically described as follows.

(1) *Eucommia ulmoides* was subjected to extraction With a 85% ethanol solution in a volume ratio of 1:8 under refluxing for 2 h and filtration to obtain a residue and a filtrate. The residue was subjected to extraction with deionized water twice in a volume ratio of 1:6 under refluxing each for 1 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was subjected to extraction with a 80% ethanol solution in a volume ratio of 1:8 under refluxing for 2 h and filtration to obtain a residue and a filtrate. The residue was subjected to extraction with the 80% ethanol solution twice in a volume ratio of 1:6 under refluxing each for 2 h and filtration. Filtrates were combined, concentrated and added with maltodextrin, where the maltodextrin was 10% by weight of *Rhizoma Drynariae*. Then the combined filtrate was continuously concentrated to a density of 1.2, dried at 75° C. under vacuum and sieved with a sieve of 80 mesh to produce the *Rhizoma Drynariae* extract.

(3) *Semen Cuscutae* was immersed in a 80% ethanol solution in a volume ratio of 1:8 for 0.5 h and subjected to extraction under refluxing for 2 h and filtration to obtain a residue and a filtrate. The residue was subjected to extraction with the 80%) ethanol solution in a volume ratio of 1:6 under refluxing twice each for 1 h. Filtrates were combined, concentrated to a density of 1.12-1.15 and subjected to spray drying at 180-200° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 80:5:5 to produce the traditional Chinese medicine composition.

Example 6

Provided herein was a method of preparing a traditional Chinese medicine for improving bone health, which was specifically described as follows.

(1) *Eucommia ulmoides* was subjected to extraction With a 85% ethanol solution in a volume ratio of 1:8 under refluxing for 2 h and filtration to obtain a residue and a filtrate. The residue was subjected to extraction with deionized water twice in a volume ratio of 1:6 under refluxing each for 1 h and filtration. Filtrates were combined, concentrated and added with maltodextrin, where the maltodextrin was 5% by weight of *Eucommia ulmoides*. The combined filtrate was continuously concentrated to a density of 1.15-1.2, dried at 75° C. under vacuum and sieved with a sieve of 80 mesh to produce the *Eucommia ulmoides* extract.

(2) *Rhizoma Drynariae* was subjected to extraction with a 80% ethanol solution in a volume ratio of 1:8 under refluxing for 2 h and filtration to obtain a residue and a filtrate. The residue was subjected to extraction with the 80% ethanol solution twice in a volume ratio of 1:6 under refluxing each for 2 h and filtration. Filtrates were combined, concentrated and added with maltodextrin, where the maltodextrin was 10% by weight of *Rhizoma Drynariae*. Then the combined filtrate was continuously concentrated to a density of 1.2, dried at 75° C. under vacuum and sieved with a sieve of 80 mesh to produce the *Rhizoma Drynariae* extract.

(3) *Semen Cuscutae* was immersed in a 80% ethanol solution in a volume ratio of 1:8 for 0.5 h and subjected to extraction under refluxing for 2 h and filtration to obtain a residue and a filtrate. The residue was subjected to extraction with the 80% ethanol solution in a volume ratio of 1:6 under refluxing twice each for 1 h. Filtrates were combined, concentrated to a density of 1.12-1.15 and subjected to spray drying at 180-200° C. The dried product was sieved with a sieve of 80 mesh to produce the *Semen Cuscutae* extract.

(4) The *Eucommia ulmoides* extract, the *Rhizoma Drynariae* extract and the *Semen Cuscutae* extract were mixed uniformly in a weight ratio of 65:30:5 to produce the traditional Chinese medicine composition.

Example 7

Provided herein was a method of detecting the activity of per unit of individual extract in the traditional Chinese medicine composition for improving bone health, which was specifically described as follows.

The total flavonoids in the extracts were determined by ultraviolet spectrophotometry.

Preparation of Reference Sample 10 mg, of rutin standard was accurately weighed, transferred to a 50 mL volumetric flask, added with methanol to the volume and mixed uniformly to produce a 0.2 mg/mL mother liquor.

0 mL, 1 mL, 2 mL, 4 mL and 8 mL of the mother liquor were respectively added to five 25 mL test tubes with a stopper and diluted with pure water to 10 mL.

Preparation of Test Sample 0.1 g of each extract (*Eucommia ulmoides*, *Rhizoma Drynariae* and *Semen Cuscutae*) was accurately weighed, dissolved with 50 mL of methanol and subjected, to ultrasonication for 1 h to produce an extract solution. 3 mL of the extract solution was transferred to a 25 mL test tube with a stopper and diluted to 10 mL with water.

Each reference sample and the test sample were respectively added with 1 mL of 5% $NaNO_2$ solution and subjected to standing for 6 min. Then each, reaction mixture was added with 1 mL of a 10% $Al(NO_3)_3$ solution, subjected to standing for 6 min, added with 1 mL of a 1 mol/L NaOH solution and diluted to 25 mL with distilled water for determination.

Test results were listed in detail in Tables 1 and 2, where an initial concentration of the rutin reference sample (purity: 94.9%) was 0.2076 mg/mL.

TABLE 1

Absorbance(Abs) of reference samples

| Volume of reference samples (mL) | Concentration (mg/mL) | Abs |
|---|---|---|
| 1 | 0.0197 | 0.093 |
| 2 | 0.0393 | 0.193 |
| 4 | 0.0787 | 0.403 |
| 8 | 0.1574 | 0.843 |

A standard curve was plotted with $y=5.4633x-0.02$ and $R^2=0.9997$.

TABLE 2

Absorbance and concentration of test samples

| Sample | Weight/g | Abs | Concentration (mg/g) | Average (mg/g) | Percentage (%) |
|---|---|---|---|---|---|
| *Eucommia ulmoides* extract | 0.1319 | 0.421 | 102.00 | 101.77 | 10.18 |
|  |  | 0.419 | 101.53 |  |  |
| *Rhizoma Drynariae* extract | 0.1361 | 0.239 | 58.05 | 57.72 | 5.77 |
|  |  | 0.236 | 57.38 |  |  |
| *Semen Cuscutae* extract | 0.1375 | 0.285 | 67.67 | 67.67 | 6.77 |
|  |  | 0.285 | 67.67 |  |  |

Described below were the common preparations of the traditional Chinese medicine composition provided herein when applied to the preparation of health food.

Example 8

The *Eucommia ulmoides* extract, *Rhizoma Drynariae* extract and *Semen Cuscutae* extract prepared in Example 1 were mixed uniformly and sieved with a sieve of 80 mesh to produce a traditional Chinese medicine composition. Then the composition was mixed uniformly with starch and magnesium stearate, pressed into tablets and film-coated to produce final tablets.

Example 9

The liquid extracts prepared in Example 1 were mixed uniformly, decoded to 1 g/mL, and transferred to a beaker, to which sucrose, starch and dextrin Were introduced and mixed uniformly to produce a mixture. When the mixture was kneaded into a dough and dispersed when touched, granules that can not pass through the 20-mesh sieve and 80-mesh sieve but can pass the 10-mesh sieve Were collected and dried in an oven in time for use.

Finally, the collected granules Were dried under Vacuum to a water content of 4% to produce the traditional Chinese medicine granules.

Example 10

The extracts prepared in Example 1 were mixed uniformly and sieved with a 80-mesh sieve to produce a traditional Chinese medicine composition, which was further mixed uniformly with magnesium stearate and encapsulated at a filling amount of 0.53-0.54 g to obtain a traditional Chinese medicine capsule.

Embodiments provided herein are described in a progressive manner, and each embodiment mainly focuses on the differences from other embodiments. The same or similar parts among various embodiments can be referred to each other.

Further, the following test was performed to evaluate the efficacy of the traditional Chinese medicine composition prepared herein.

Efficacy Test

Samples: the traditional Chinese medicine (TCM) composition prepared in Example 1, a positive drug (Estradiol Valerate) and a competing drug (Caltrate).

Grouping

Female SD rats were randomly divided into sham operation group, model group, positive control group (estradiol valerate), competing drug group (Caltrate), high dose TCM composition (prepared in Example 1) group and low dose TC'M composition (prepared in Example 1) group, and 8 in each group.

Model Establishment

Female SD rats were treated by bilateral ovariectomy to establish osteoporosis model rats.

Administration

The osteoporosis model rats were subjected to intragastric administration once a day and the administration cycle lasted for 8 weeks.

Indicators

At the end of each week, each rat was fasted (water was allowed) for 12 hours to measure the weight change, observe and record the eating and mental state and the coat color and evaluate the quality of the model. Further, the vaginal epithelial cells were subjected to smear test to obtain the estrus cycle to determine whether the rats were completely ovariectomized.

After 8 weeks, the rats were sacrificed, and blood was collected from the abdominal aorta and subjected to standing for 1 hour. Then the blood sample was centrifuged to collect serum, which was detected for the bone metabolic biochemical indicators, including bone glaprotein (BGP), bone specific alkaline phosphatase (BALP), carboxyterminal propeptide of type I procollagen (PICP) and N-telopeptides of type I collagen (NTX); estrogen indicators, including serum estradiol E2 and follicle stimulating hormone (FSH); and blood biochemical indexes, including serum phosphorus and serum calcium. Moreover, the complete bilateral femurs were collected, on which the muscle tissues were, completely removed. The left femur was used for femoral mechanical testing, and the right femur was tested for related parameters such as bone density. The above experimental data was used to evaluate the efficacy of the TCM composition of the disclosure.

It should be noted that the dosage for each test group was shown as follows.

The dosage of the TCM composition was determined based on the recommended crude drug dosage in the pharmacopoeia, and 1 g of extract was obtained after the extraction.

Positive control group: 0.1 g/day for human.

Competing drug group (Caltrate): one tablet (1 g)/day and 600 mg of calcium/tablet.

High dose TCM composition group: 1 g/day for human; low dose TCM composition group: 0.5 g/day for human.

The dosage for rats was calculated as follows:

dosage for rat (daily dose for human/60)*6;

where 60 referred to body weight of human, and 6 indicated the rat coefficient.

The experimental results were presented as follows.

TABLE 3

Serum estrogen indicators of rats in different groups

| Group | Dosage (mg/kg) | E2 (pg/mL) | FSH (ng/mL) |
| --- | --- | --- | --- |
| Sham-operation | / | 67.69 ± 18.74# | 57.71 ± 25.62# |
| Model | / | 37.96 ± 11.37* | 109.22 ± 22.25* |
| Positive control | 10 | 32.45 ± 10.24* | 96.55 ± 11.84* |
| Caltrate | 60 | 39.17 ± 6.97* | 118.02 ± 35.68* |
| High dose TCM in Exa. 1 | 100 | 40.16 ± 8.82* | 111.09 ± 25.16* |
| Low dose TCM in Exa. 1 | 50 | 50.59 ± 13.76*# | 98.78 ± 25.22* |

Notes:
*indicated that there was significant difference (P < 0.05) when compared to the sham-operation group; and
indicated that there was significant difference (P < 0.05) when compared to the model group.

Figure 1:
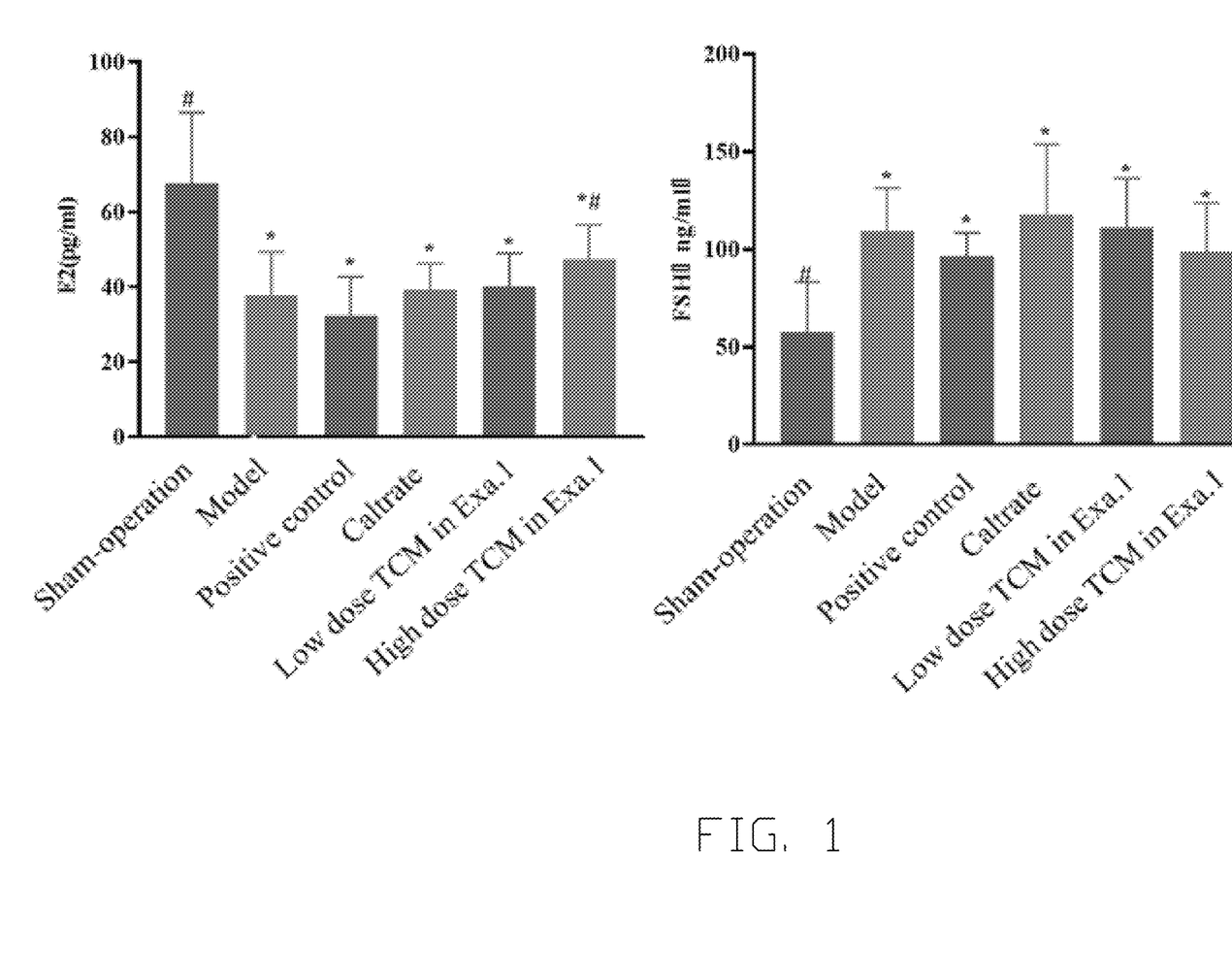
FIG. 1 shows levels of estrogen in rats from different groups.

The corresponding histogram was shown in FIG. 1. After the 8 weeks administration, the ELISA test results of the two estrogen indicators (serum estradiol E2 and FSH) revealed that compared to the model group, the low dose TCM composition group had a significantly higher E2 level (P<0.05). Therefore, it can be demonstrated that the TCM composition of the disclosure can significantly inhibit the decline of the serum E2 level in rats, and had the effect of preventing the reduction of estrogen level in menopause, preventing the bone loss.

TABLE 4

Serum biochemical indexes of rats in different groups

| Group | Dosage (mg/kg) | P (mmol/L) | Ca (mmol/L) |
| --- | --- | --- | --- |
| Sham-operation | / | 2.43 ± 0.59 | 2.42 ± 0.12 |
| Model | / | 2.38 ± 0.44 | 2.26 ± 0.25 |
| Positive control | 10 | 3.1 ± 0.53*# | 2.33 ± 0.13 |
| Caltrate | 60 | 2.34 ± 0.35 | 2.4 ± 0.09 |
| High dose TCM in Exa. 1 | 100 | 1.9 ± 0.39* | 2.31 ± 0.1 |
| Low dose TCM in Exa. 1 | 50 | 2.23 ± 0.57 | 2.19 ± 0.3 |

Notes:
*indicated that there was significant difference (P < 0.05) when compared to the sham-operation group; and
indicated that there was significant difference (P < 0.05) when compared to the model group.

Figure 2:
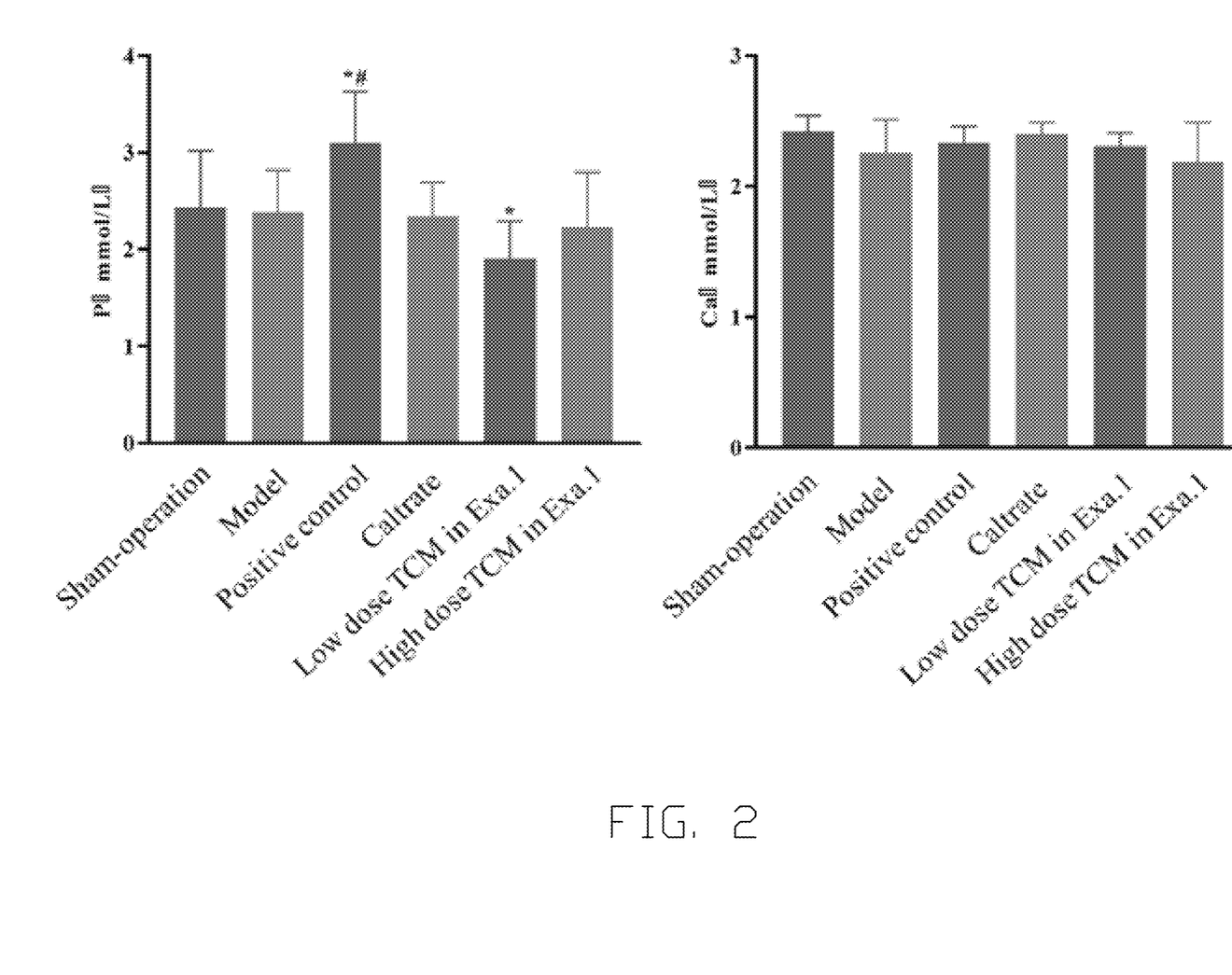
FIG. 2 illustrates detection results of blood biochemical indexes of rats from different groups.

The corresponding histogram was shown in FIG. 2. After the 8 weeks' administration, the positive control group had significantly higher serum phosphorus content than the model group and the sham-operation group (P<0.05), while the serum phosphorus content of the high dose TCM composition group was significantly lower than the sham-operation group (P<0.05). Other groups had similar serum phosphorus content. There was no significant difference among all experimental groups with respect to the serum calcium content.

TABLE 5

Bone metabolic biochemical indicators of rats in different groups

| Group | Dosage (mg/kg) | BGP (ng/mL) | BALP (pg/mL) | PICP (ng/mL) | NTX (ng/mL) |
|---|---|---|---|---|---|
| Sham-operation | / | 10.53 ± 1.78 | 861.31 ± 123.6 | 743.78 ± 94.67 | 23.31 ± 6.41 |
| Model | / | 9.97 ± 1.76 | 791.63 ± 98.35 | 686.71 ± 95.49 | 24.27 ± 3.53 |
| Positive control | 10 | 9.93 ± 2.23 | 764.2 ± 123.81 | 739.33 ± 175.34 | 26.92 ± 5.68 |
| Caltrate | 60 | 9.11 ± 1.29 | 762.45 ± 79.35 | 797.25 ± 136.34 | 23.64 ± 2.58 |
| High dose TCM in Exa. 1 | 100 | 10.57 ± 1.12 | 770.2 ± 129.17 | 747.88 ± 173.12 | 26.17 ± 2.4 |
| Low dose TCM in Exa. 1 | 50 | 11.1 ± 1.24 | 791.45 ± 106.44 | 795.06 ± 104.06 | 25.51 ± 3.96 |

Notes:
* indicated that there was significant difference ($P < 0.05$) when compared to the sham-operation group; and
indicated that there was significant difference ($P < 0.05$) when compared to the model group.

Figure 3:
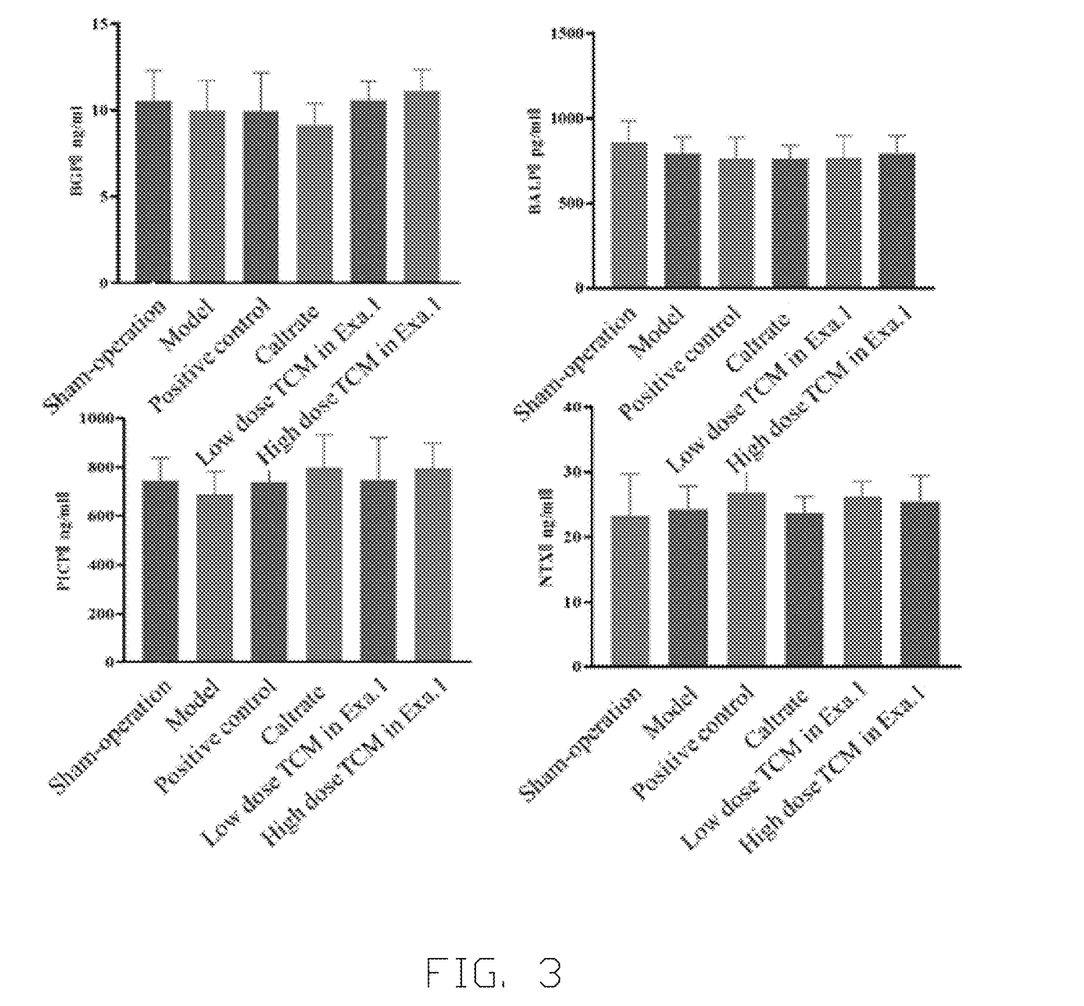
FIG. 3 illustrates detection results of bone metabolic biochemical markers of rats from different groups.

The corresponding histogram, was shown in FIG. 3. After the 8 weeks' administration, the ELISA test results showed that there was no significant difference among all experimental groups with respect to the four bone metabolic indicators (BGP, BALP, PICP and NTX).

TABLE 6

Bone density parameters of rats in different groups

| Group | Dosage (mg/kg) | BMD (g/cm$^2$) | BV/TV (%) | Tb. N (1/mm) | Tb. Sp (μm) |
|---|---|---|---|---|---|
| Sham-operation | / | 0.257 ± 0.057# | 22.5 ± 4# | 3.25 ± 0.571# | 258.837 ± 77.079# |
| Model | / | 0.186 ± 0.049* | 15.56 ± 4.14* | 2.195 ± 0.53* | 500.657 ± 155.844* |
| Positive control | 10 | 0.198 ± 0.051* | 16.863 ± 5.237* | 2.392 ± 0.809* | 455.6 ± 182.901* |
| Caltrate | 60 | 0.165 ± 0.048* | 13.826 ± 4.365* | 1.983 ± 0.588* | 535.106 ± 176.152* |
| High dose TCM in Exa. 1 | 100 | 0.246 ± 0.065# | 20.083 ± 5.255 | 2.758 ± 0.711 | 346.449 ± 116.986 |
| Low dose TCM in Exa. 1 | 50 | 0.181 ± 0.049* | 15.582 ± 4.905* | 2.248 ± 0.719* | 492.541 ± 178.987* |

Notes:
*indicated that there was significant difference ($P < 0.05$) when compared to the sham-operation group; and
indicated that there was significant difference ($P < 0.05$) when compared to the model group.

Figure 4:
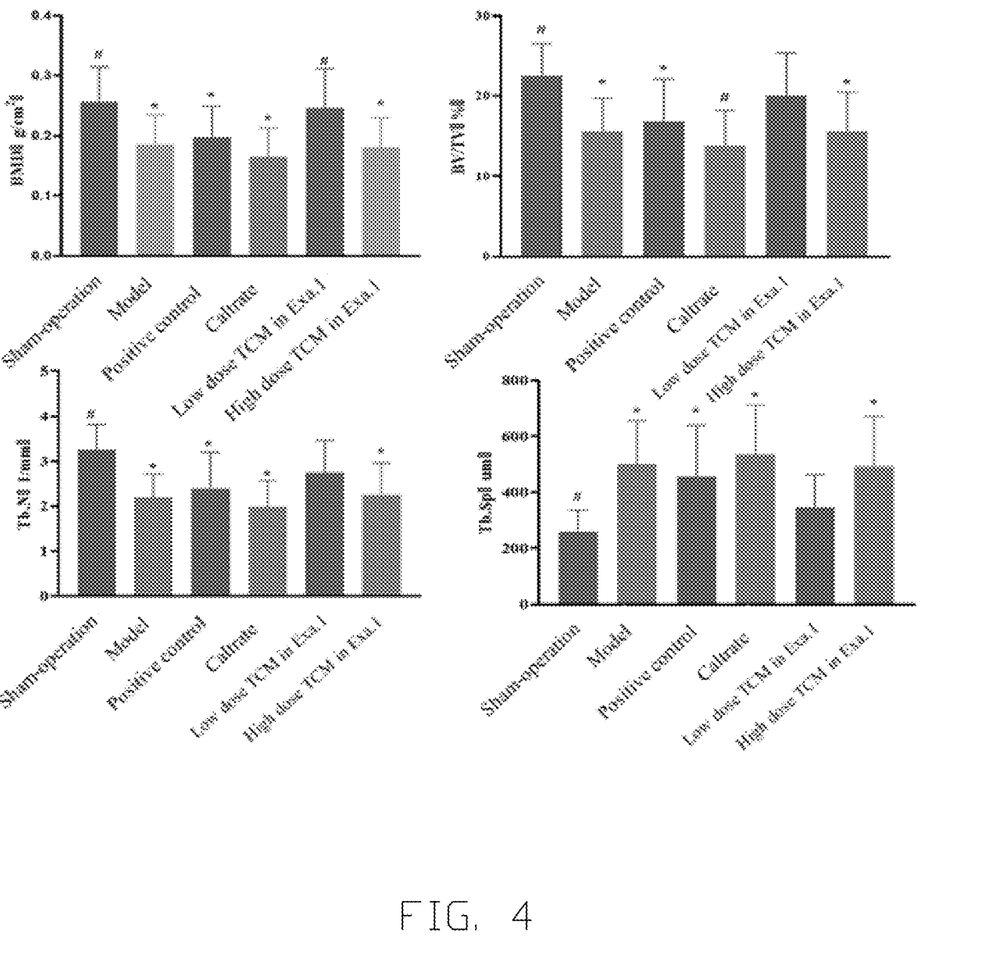
FIG. 4 illustrates detection results of bone density-associated markers of rats from different groups.

The corresponding histogram was shown in FIG. 4. It can be seen through the analysis of parameters of the bone tissue microstructure at the femoral metaphysis region of rats that compared to the sham-operation group, the model group had significantly lower bone mineral density (BMD), bone volume fraction (BV/TV) and (Tb.N) ($P<0.05$) and significantly higher trabecular separation/spacing (Tb.Sp) ($P<0.05$); compared to the model group, the high dose TCM composition group had significantly increased bone mineral density ($P<0.05$), and exhibited an increasing trend in the bone volume fraction and the trabecular number and a decreasing trend in the trabecular separation/spacing. The above results demonstrated that the composition provided herein can improve the bone density, and thus it had a certain, preventive effect on osteoporosis.

TABLE 7

Mechanical indexes of rats in different groups

| Group | Dosage (mg/kg) | Load/N |
|---|---|---|
| Sham-operation | / | 138.16 ± 26.71# |
| Model | / | 93.13 ± 17.74* |
| Positive control | 10 | 109.67 ± 26.78* |
| Caltrate | 60 | 104.06 ± 19.52* |
| High dose TCM in Exa. 1 | 100 | 126.6 ± 12.57# |
| Low dose TCM in Exa. 1 | 50 | 89.98 ± 23.41* |

Notes:
*indicated that there was significant difference ($P < 0.05$) when compared to the sham-operation group; and
indicated that there was significant difference ($P < 0.05$) when compared to the model group.

Figure 5:
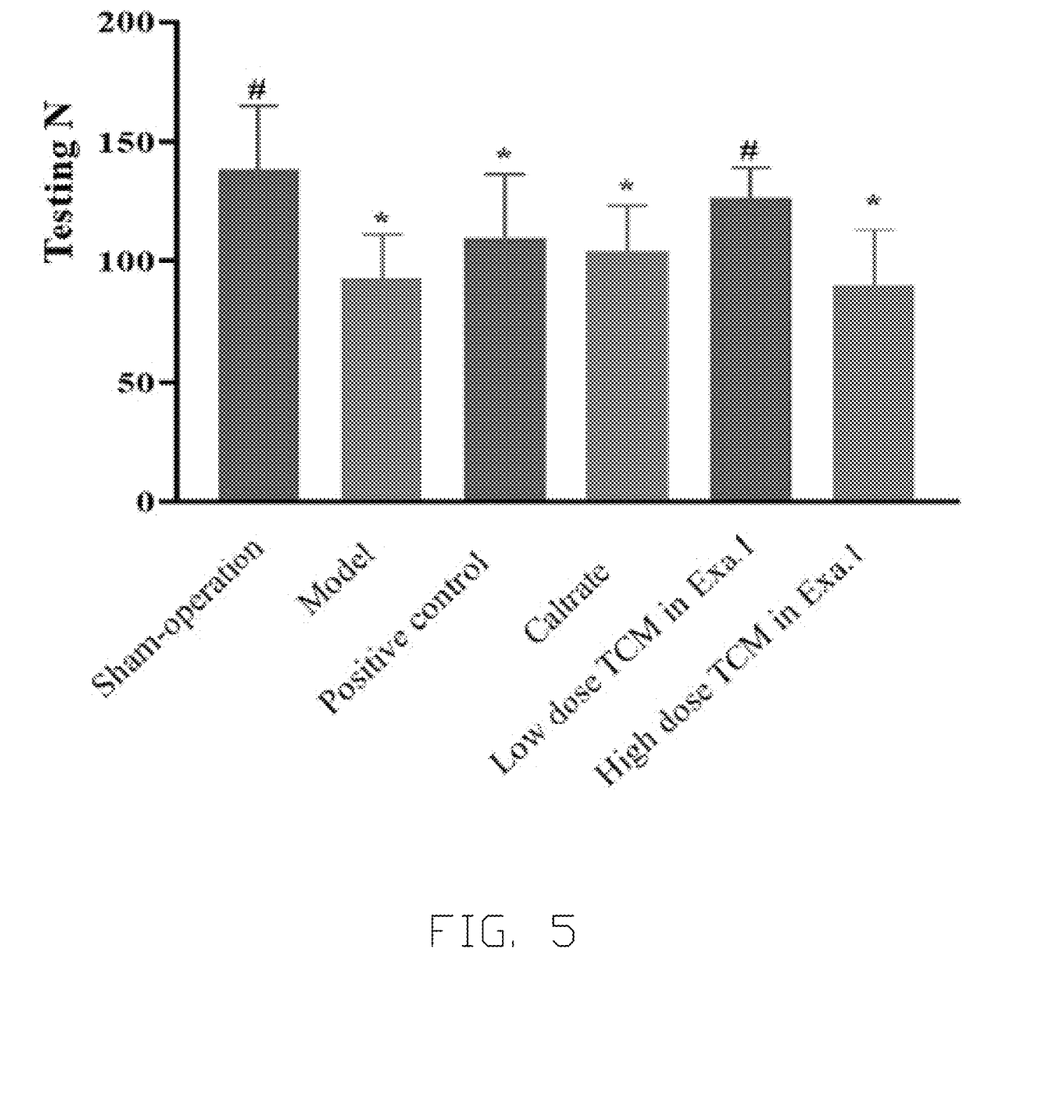
FIG. 5 shows testing results of mechanical indexes of rats from different groups.

The corresponding histogram was shown in FIG. 5. It can be seen from the biomechanical test results of rat femurs that compared to the sham-operation group, the model group had significantly lower maximum load ($P<0.05$); the high dose TCM composition group was significantly higher than the model group in the maximum load ($P<0.05$). The above results indicated that the composition prepared herein, can reduce the risk of fracture and had a certain preventive effect on the osteoporosis.

Based on the analysis of the above experimental results, it can be concluded that compared with the model group, the composition provided herein can significantly inhibit the decrease in the serum E2 level, increase bone density and the maximum load of femur in rats. Therefore, the composition of the disclosure had the effects of preventing the decline of estrogen level in menopause, preventing the sexual organ atrophy, improving sexual function, inhibiting bone loss and increasing the bone density and can be used to prevent osteoporosis and improve bone health.

Described above are merely illustrative of the invention to enable those skilled in the art to implement or use the invention, and are not intended to limit the invention. It should be understood that any modification, replacement and change made by those skilled in the art without, departing from the spirit of the invention should fall within the scope of the invention.

What is claimed is:

1. A method of preparing a traditional Chinese medicine composition for improving bone health, comprising:

subjecting *Eucommia ulmoides*, *Rhizoma Drynariae* and *Semen Cuscutae* to extraction, concentration and drying to produce *Eucommia ulmoides* extract, *Rhizoma Drynariae* extract and *Semen Cuscutae* extract, respectively; and mixing the *Eucommia ulmoides* extract, the *Rhizoma Drynariae* extract and the *Semen Cuscutae* extract uniformly to produce the traditional Chinese medicine composition;

wherein the method specifically comprises:

(1) subjecting *Eucommia ulmoides*, *Rhizoma Drynariae* and *Semen Cuscutae* to extraction respectively with an ethanol solution under refluxing and filtration; subjecting a residue to extraction with a solvent and filtration; and combining filtrates to obtain a crude *Eucommia ulmoides* extract, a crude *Rhizoma Drynariae* extract and a crude *Semen Cuscutae* extract, respectively;

(2) subjecting the crude *Eucommia ulmoides* extract, the crude *Rhizoma Drynariae* extract and the crude *Semen Cuscutae* extract to concentration; introducing maltodextrin to the concentrated *Eucommia ulmoides* extract and the concentrated *Rhizoma Drynariae* extract, respectively; wherein the maltodextrin introduced to the concentrated *Eucommia ulmoides* extract is 5% by weight of *Eucommia ulmoides* extract; the maltodextrin introduced to the concentrated *Rhizoma Drynariae* extract is 10% by weight of *Rhizoma Drynariae* extract;

spray drying or vacuum drying and sieving to produce the *Eucommia ulmoides* extract, the *Rhizoma Drynariae* extract and the *Semen Cuscutae* extract; and (3) mixing the *Eucommia ulmoides* extract, the *Rhizoma Drynariae* extract and the *Semen Cuscutae* extract uniformly in a weight ratio of (60-80):(15-30):(5-10) to produce the traditional Chinese medicine composition.

2. The method of claim 1, wherein in step (1), a volume ratio of *Eucommia ulmoides* to the ethanol solution is 1:(5-20); a volume ratio of *Rhizoma Drynariae* to the ethanol solution is 1:(5-20); a volume ratio of *Semen Cuscutae* to the ethanol solution is 1:(5-20); and the extraction of *Eucommia ulmoides*, *Rhizoma Drynariae* and *Semen Cuscutae* is performed at 80-100° C. 1-3 times each for 1-3 h, respectively.

3. The method of claim 1, wherein in step (1), a volume ratio of the solvent to the residue is (6-8):1; and the extraction of the residue is performed at 80-100° C. under refluxing 1-3 times each for 1-2 h.

4. The method of claim 2, wherein in step (1), a volume ratio of the solvent to the residue is (6-8):1; and the extraction of the residue is performed at 80-100° C. under refluxing 1-3 times each for 1-2 h.

5. The method of claim 1, wherein in step (2), the spray drying is performed at 180-200° C.; or the vacuum drying is performed at 50-100° C., and the sieving is performed using a sieve of 60-80 mesh.

* * * * *